US00PP10530P

United States Patent [19]

Pouw

[11] Patent Number: Plant 10,530

[45] Date of Patent: Aug. 4, 1998

[54] HYBRID TEA ROSE PLANT NAMED 'RUICONTI'

[75] Inventor: A. A. Pouw, Pl De Kwakel, Netherlands

[73] Assignee: De Ruiter's Nieuwe Rozen B.V., Pl De Kwakel, Netherlands

[21] Appl. No.: 789,830

[22] Filed: Jan. 28, 1997

[51] Int. Cl.[6] ..... A01H 5/00

[52] U.S. Cl. ..... Plt./15

[58] Field of Search ..... Plt./15

*Primary Examiner*—Howard J. Locker
*Attorney, Agent, or Firm*—Christie, Parker & Hale, LLP

[57] ABSTRACT

A new variety of hybrid tea rose plant producing deep yellow flowers of good form and suitable for growing under glass.

1 Drawing Sheet

BACKGROUND OF THE INVENTION

The present invention relates to a new and distant variety of rose plant of the hybrid tea rose class which was created by crossing undistributed, unnamed and unpatented seedlings as seed and pollen parents in De Kwakel, Holland. The varietal denomination of the new variety is 'Ruiconti'. The new variety was isolated and asexually reproduced by budding in De Kwakel, Holland.

SUMMARY OF THE INVENTION

Among the novel characteristics possessed by this new variety which distinguish it from its parents and all other varieties of which I am aware are its attractive deep yellow flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (RHSCC) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.
Class: Hybrid Tea.

As can be seen in the accompanying detail illustration there is shown a new shoot, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed.

The following further horticultural description is based on observations made of specimens grown under glass in De Kwakel, Holland.

FLOWER

Blooming habit: Nearly continuous.

A. Bud:

(1) *Size.*—Medium, about 4 cm long and about 3 cm wide.

(2) *Form.*—Ovate (shape of longitudinal section just before separation of sepals); urn-shaped after sepals part.

(3) *Color.*—As sepals divide, near 15B.

(4) *Sepals.*—Longer than green bud, foliated, upper surface coloration near 144A to 144B, under surface coloration near 144B.

(5) *Peduncle.*—Long: Strength-erect, very strong. Color — near 147A to 147B, few hairs and prickles, about 10 cm.

B. Bloom:

*Flower.*—Medium; viewed from above — round; viewed from side — (a) upper part of fully opened flower, flat; (b) lower part of fully opened flower, flat.

(1) *Size.*—Average size when fully expanded — about 9 cm.

(2) *Borne.*—Singly, one to a stem.

(3) *Form.*—Pointed center, exhibition type, spiral imbricated, outer petals reflex to points.

(4) *Petalage.*—Fully double, about 25, about 19 petaloids about 0.5×0.5 cm, very crinkled.

(5) *Color.*—After sepals part and petals unfurl, near 13B; flower color is near 15A to 16A; petal undersurface near 13C; point of petal attachment, near 13B; overall tonality from a distance is attractive deep yellow.

(6) *Peduncle.*—Generally smooth.

(7) *Fragrance.*—Sweet, fruity.

(8) *Length of stems**.—About 70 cm.

(9) *Production**.—About 160/m$^2$/yr.

*Average, depends upon circumstances of cultivation.

Petals:

(1) *Texture.*—Crisp.

(2) *Appearance.*—Inside velvety and outside satiny.

(3) *Form and size.*—Broad, large, absent or very weak undulation of margin.

(4) *Arrangement.*—Regularly arranged, imbricated.
(5) *Petaloids.*—Several, about 19.
(6) *Lasting quality.*—Long-lasting quality on plant and after cutting, vaselife is about 12 to 14 days. Bloom on plant lasts about 10–12 days and then the petals drop.

REPRODUCTIVE ORGANS

A. Stamens, filaments and anthers:
*Arrangement and color.*—Regularly arranged around styles; color of filaments — yellow.
B. Pollen:
*Color.*—Near 13A.
C. Styles: Long, stigma above mouth of receptacle, yellows.
D. Stigmas: Yellow, positioned below anthers
E. Hip: Funnel-shaped; medium seed vessel at petal fall, orange yellow, about 1.5 cm

PLANT

A. Form: Narrow to bushy, tall, average disease resistance.
B. Growth: Vigorous, about 1.8 m in height, about 0.5 m in width.
C. Foliage: Compound 3, 5 and 7 leaflets.
(1) *Size.*—Medium width and length, about 15–17 cm.
(2) *Quantity.*—Abundant.
(3) *Color:*Foliage—foliage color of upperside of leaf near 139 A, foliage color of underside of leaf near 139B; weak anthocyanin coloration (shoot about 20 cm long); mature leaf color — upperside near 147A to 139A, underside 139B.
(4) *Shape.*—Broad oval.
(5) *Texture.*—Upper side is weak glossy; underside is matte.
(6) *Edge.*—Serrate.
(7) *Serration.*—Ordinary, acuminate apices.
(8) *LeafStem.*—Color — medium green, near 147A to 147B.
(9) *Stipules.*—Short, simple, medium green, distinct auricle.
(10) *Leaflets.*—Cross section — slight concave: absent or very weak undulation of margin; terminal leaflet — medium length and width; blade about 9 to 10 cm long and 5 to 6 cm wide, obtuse base.
D. Wood:
(1) *New wood.*—Color — young shoots have weak to medium anthocyanin; coloration — near 144A, small prickles, bronze red purple to reddish brown.
(2) *Old wood.*—Color — near 147A to 147B with brownish cast.
E. Prickles (thorns):
(1) *Prickles.*—Present; quantity (main stalk) — many; shape of lower side — deep concave; Length — short prickles many or very many, long prickles medium; Color — near 179A to 179B; Position — irregular.

Disease resistance: Average resistance to powdery and downey mildew.

What is claimed is:

1. A new and distinct variety of rose plant of the hybrid tea rose class, substantially as shown and described.

* * * * *

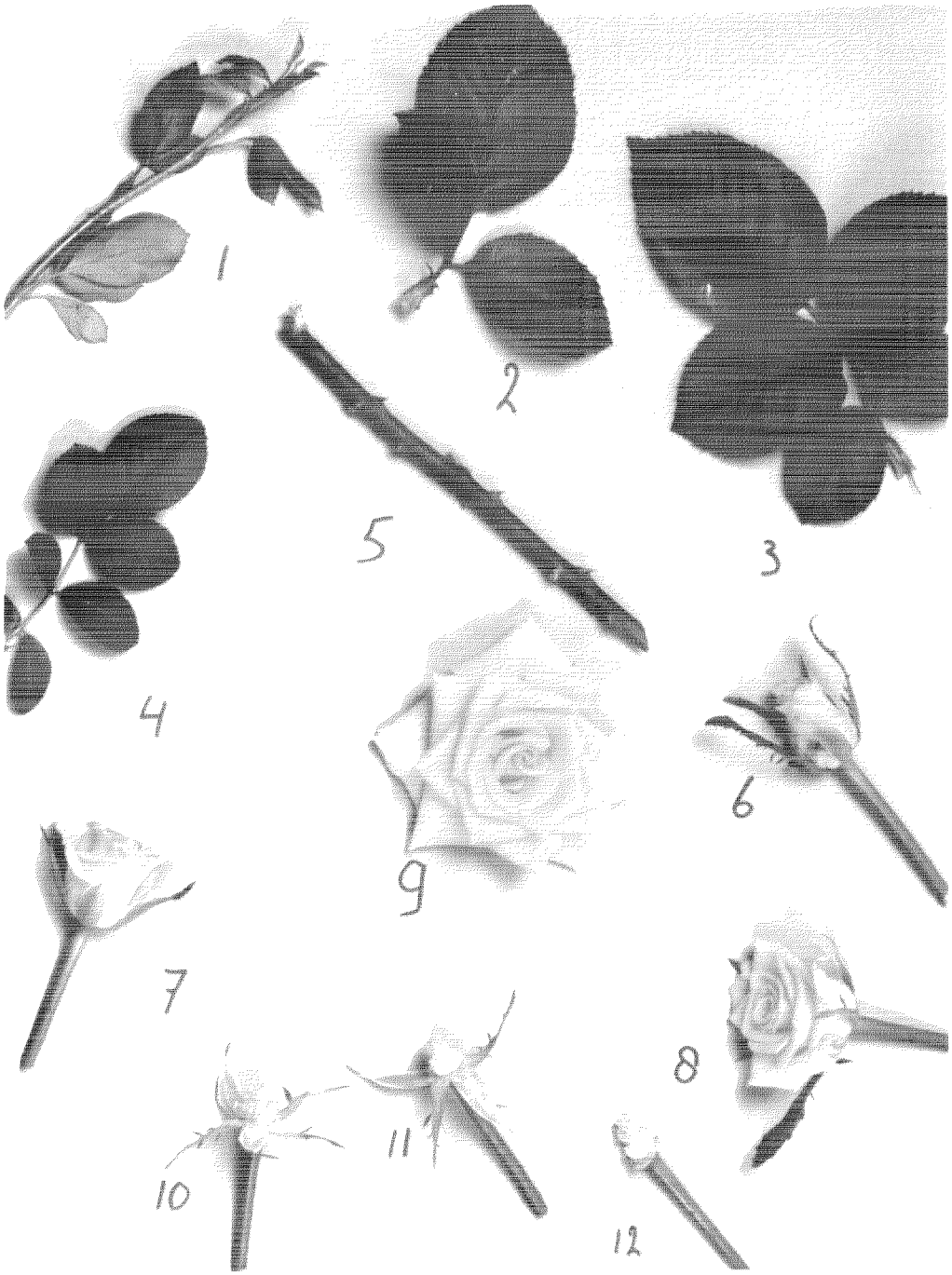
1
2
3
4
5
6
7
8
9
10
11
12

UNITED STATES PATENT AND TRADEMARK OFFICE

CERTIFICATE OF CORRECTION

PATENT NO. : Plant 10,530
DATED : August 4, 1998
INVENTOR(S) : A. A. Pouw

It is certified that error appears in the above-identified patent and that said Letters Patent is hereby Column 4, line 6, change "(8) *LeafStem*" to -- (8) *Leaf—Stem:* --.

Signed and Sealed this

Seventh Day of March, 2000

*Attest:*

*Attesting Officer*

Q. TODD DICKINSON

*Commissioner of Patents and Trademarks*